US012051758B2

United States Patent
Haiberger et al.

(10) Patent No.: US 12,051,758 B2
(45) Date of Patent: Jul. 30, 2024

(54) OPTOELECTRONIC SENSOR ARRANGEMENT AND OPTICAL MEASURING METHOD

(71) Applicant: OSRAM Opto Semiconductors GmbH, Regensburg (DE)

(72) Inventors: Luca Haiberger, Regensburg (DE); Daniel Richter, Bad Abbach (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 474 days.

(21) Appl. No.: 17/425,596

(22) PCT Filed: Jan. 29, 2020

(86) PCT No.: PCT/EP2020/052121
§ 371 (c)(1),
(2) Date: Jul. 23, 2021

(87) PCT Pub. No.: WO2020/160973
PCT Pub. Date: Aug. 13, 2020

(65) Prior Publication Data
US 2022/0102562 A1 Mar. 31, 2022

(30) Foreign Application Priority Data

Feb. 8, 2019 (DE) .......................... 102019103155.9

(51) Int. Cl.
*H01L 31/0232* (2014.01)
*G02B 6/42* (2006.01)
(Continued)

(52) U.S. Cl.
CPC ...... *H01L 31/02327* (2013.01); *G02B 6/4214* (2013.01); *G02B 6/4215* (2013.01);
(Continued)

(58) Field of Classification Search
CPC ............ H01L 31/02327; H01L 31/173; H01L 31/0203; H01L 25/167; G02B 6/4214;
(Continued)

(56) References Cited

U.S. PATENT DOCUMENTS

| 5,189,500 A | 2/1993 | Kusunoki |
| 6,232,714 B1 | 5/2001 | Shen et al. |

(Continued)

FOREIGN PATENT DOCUMENTS

| DE | 4444470 A1 | 5/1996 |
| JP | 2018019013 A | 2/2018 |

(Continued)

OTHER PUBLICATIONS

Amanzadeh, M. et al., "Recent Developments in Fibre Optic Shape Sensing," Elsevier, Measurement 128, Jun. 20, 2018, 19 pages.

(Continued)

*Primary Examiner* — Patricia D Valenzuela
(74) *Attorney, Agent, or Firm* — Slater Matsil, LLP

(57) ABSTRACT

In an embodiment an optoelectronic sensor arrangement includes a carrier substrate, an illuminating device, a frequency-selective optical element and a photodetector, wherein the illuminating device and the photodetector form a stacked arrangement on or with the carrier substrate, wherein the frequency-selective optical element is arranged between the illuminating device and the photodetector, wherein the photodetector is arranged in a cavity of the carrier substrate which is covered by the illuminating device and/or the frequency-selective optical element, and wherein the frequency-selective optical element includes a divider mirror and an optical filter.

18 Claims, 3 Drawing Sheets

(51) Int. Cl.
*H01L 31/173* (2006.01)
*H01L 25/16* (2023.01)
*H04B 10/40* (2013.01)

(52) U.S. Cl.
CPC .......... *H01L 31/173* (2013.01); *H01L 25/167* (2013.01); *H04B 10/40* (2013.01)

(58) Field of Classification Search
CPC ....... G02B 6/4215; A61B 5/0059; A61B 5/11; A61B 5/6804; A61B 2562/0233; G01D 5/35358; H04B 10/40
See application file for complete search history.

(56) References Cited

U.S. PATENT DOCUMENTS

| | | | |
|---|---|---|---|
| 6,745,061 | B1 | 6/2004 | Hicks et al. |
| 9,836,165 | B2 | 12/2017 | Nho et al. |
| 2005/0107024 | A1 | 5/2005 | Quattrini et al. |
| 2009/0034982 | A1* | 2/2009 | Deng ..................... H04B 10/40 398/139 |
| 2017/0146417 | A1 | 5/2017 | LeBlanc |
| 2019/0331473 | A1* | 10/2019 | Johnson ............. G01B 9/02015 |

FOREIGN PATENT DOCUMENTS

| | | |
|---|---|---|
| KR | 20140105885 A | 9/2014 |
| WO | 2017218467 A1 | 12/2017 |

OTHER PUBLICATIONS

Dandin, M. et al., "Optical Filtering Technologies for Integratged Fluorescence Sensors," The Royal Society of Chemistry 2007, Lab Chip, Jul. 10, 2007, 23 pages.

Lopez-Higuera, J.M. et al., "Fiber Optic Sensors in Structural Health Monitoring," Journal of Lightwave Technology, vol. 29, No. 4, Feb. 15, 2011, 22 pages.

* cited by examiner

OPTOELECTRONIC SENSOR ARRANGEMENT AND OPTICAL MEASURING METHOD

This patent application is a national phase filing under section 371 of PCT/EP2020/052121, filed Jan. 29, 2020, which claims the priority of German patent application 102019103155.9, filed Feb. 8, 2019, each of which is incorporated herein by reference in its entirety.

TECHNICAL FIELD

The present invention relates to an optoelectronic sensor arrangement, an optical measuring method, and an optical measuring device comprising an elastic fiber-optic element.

BACKGROUND

Optoelectronic sensor arrangements grouping an illuminating means, in particular an optoelectronic component such as a photodiode or a laser diode, with a photodetector on a carrier substrate in a cluster are known. For example, U.S. Pat. No. 9,836,165 B2 describes the juxtaposition of RGB illuminating means, IR emitters and optical detectors for capturing a fingerprint on a display. Further, U.S. Pat. No. 6,745,061 B1 and US Patent Application No. 2005/0107024 A1 disclose sensor arrangements that detect electromagnetic radiation reflected back from a target with a photodetector positioned adjacent to a radiation emitting unit that illuminates the target. The arrangement of the associated illuminating means and photodiodes in spatially separated substrate cavities or the use of filter components to prevent direct irradiation from the illuminating means to the photodetector result in transverse dimensions of the optoelectronic sensor arrangements that make coupling with a fiber-optic element difficult.

Furthermore, stacked optoelectronic illuminating means are known. By way of example, reference is made to U.S. Pat. No. 6,232,714 B1, which discloses a stacked arrangement with OLEDs. Further, U.S. Pat. No. 5,189,500 A describes a multilayer semiconductor device with a sensor arrangement on a first substrate side and an associated display unit on the opposite substrate side. The aforementioned semiconductor stack arrangements are not suitable for forming a small-scale optoelectronic sensor arrangement which illuminates an object and detects backscattered, frequency-shifted radiation from the object.

SUMMARY

Embodiments provide a small-size optoelectronic sensor arrangement comprising an illuminating means and a photodetector, the photodetector being configured for measuring frequency-shifted scattered light. Further embodiments provide optical measuring device comprising an elastic fiber-optic element and a coupled compact optoelectronic sensor arrangement. Other embodiments provide an optical measuring method which detects the backscattered radiation in a fiber-optic element.

Embodiments proceed from an optoelectronic sensor arrangement on a carrier substrate with an illuminating means and a photodetector. To achieve a cluster arrangement in a particularly small space, especially with regard to the transverse extension, the illuminating means and the photodetector form a stacked arrangement on or with the carrier substrate, wherein a frequency-selective optical element is arranged between the illuminating means and the photodetector. Advantageously, the photodetector is located rearwardly of the illuminating means such that the electromagnetic radiation received by the photodetector passes through the illuminating means before reaching the photodetector. Furthermore, it is preferred that the frequency-selective optical element is configured to shield the photodetector from the electromagnetic radiation emitted by the illuminating means.

The illuminating means of the optoelectronic sensor arrangement may be an optoelectronic surface emitter or an optoelectronic edge emitter forming a light emitting diode or a laser diode. A stacked arrangement of several optoelectronic components to form the illuminating means is also conceivable.

Advantageously, the illuminating means is configured for coupling into a fiber-optic element. Preferably, the illuminating means is embedded in a reflecting material, in particular in such a way that the reflecting material surrounds the illuminating means at its side walls and/or comprises a concave mirror shape, in order to intensify the radiation characteristic in the direction of the surface normal of the carrier substrate and to improve the light coupling to the fiber-optics. Preferably, the upper side of the illuminating means facing the fiber-optics remains free of the reflective material coating provided for the lateral cladding. In addition, micro-optics can be used for coupling the illuminating means and the fiber-optic element.

For the optical measurement method, the electromagnetic radiation generated by an illuminating means arranged on a carrier substrate is coupled into a fiber-optic element and at least part of the backscattered radiation in the fiber-optic element is returned to a photodetector. Thereby, the wavelength of the backscattered radiation depends in particular on the strain state of the fiber-optic element.

Preferably, the frequency-selective optical element of the stacked arrangement of the optoelectronic sensor arrangement exclusively transmits electromagnetic radiation which is frequency-shifted with respect to the electromagnetic radiation emitted by the illuminating means. Thereby, for an advantageous embodiment, the frequency-selective optical element comprises a divider mirror and/or an optical filter. The divider mirror may be a Bragg mirror whose maximum reflectivity is for a wavelength corresponding to the wavelength $\lambda_e$ of the maximum of the spectral distribution of the electromagnetic radiation emitted by the illuminating means. For an embodiment of the frequency-selective optical element with an optical filter, the latter is preferably a long pass filter whose cut-on wavelength $\lambda_c$ is greater than the wavelength $\lambda_e$ of the maximum of the spectral distribution of the electromagnetic radiation emitted by the illuminating means.

For a preferred embodiment of the optoelectronic sensor arrangement, the illuminating means is in the direction of its main radiation direction arranged above the photodetector. The overlapping direction of the stacked arrangement is oriented in the direction of the surface normal of the carrier substrate. In addition, the stacked arrangement is surrounded by the carrier substrate and/or an electromagnetic radiation-absorbing material in such a way that the radiation received by the photodetector passes exclusively through the frequency-selective optical element.

For an advantageous embodiment of the optoelectronic sensor arrangement, the illuminating means and the photodetector lie on the same side of the carrier substrate and form a stacked arrangement on the latter in combination with an intermediate frequency-selective optical element. For shielding, an arrangement of the photodetector is provided in a cavity of the carrier substrate which is covered by the illuminating means and/or the frequency-selective optical element.

For a further preferred embodiment, the illuminating means and the photodetector are positioned on different sides of the carrier substrate, whereby an optical window is arranged in the carrier substrate between the illuminating means and the photodetector, through which the scattered light to be detected reaches the photodetector. The chosen arrangement of illuminating means and photodetector simplifies the mounting, especially the contacting of the illuminating means and the photodetector in case of a design as flip-chip mounting elements.

An optical measuring device comprising a fiber-optic element, in particular an elastic fiber-optic element, and a compact optoelectronic sensor arrangement coupled thereto can be worn by a user on the body or incorporated in an article of clothing, in particular for measuring movements. In addition to the small size and the associated material savings, the optical encapsulation of the photodetector in the stacked arrangement improves the signal-to-noise ratio of the optoelectronic sensor arrangement.

BRIEF DESCRIPTION OF THE DRAWINGS

In the following, exemplary embodiments of the invention are explained in connection with figure representations. These show, in each case schematically, the following.

DETAILED DESCRIPTION OF ILLUSTRATIVE EMBODIMENTS

Figure 1:
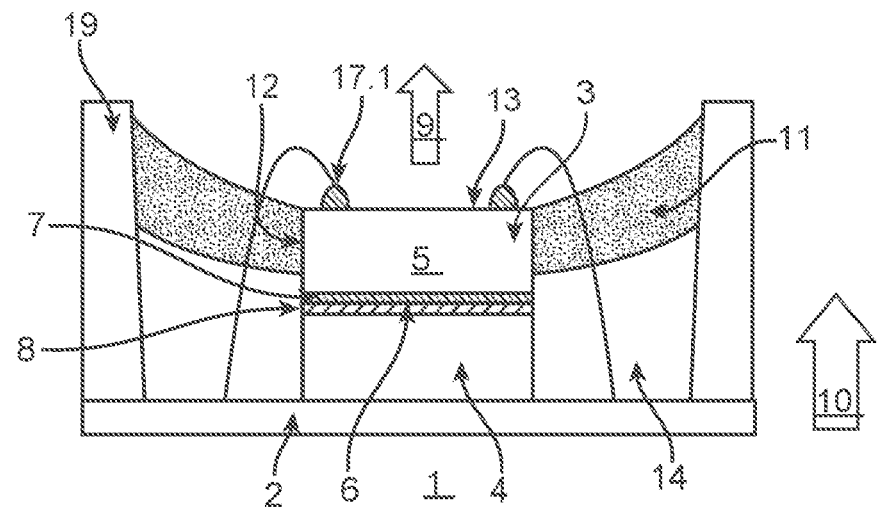
FIG. 1 shows a cross-sectional view of an optoelectronic sensor arrangement according to embodiments.

FIG. 1 represents a first embodiment of the optoelectronic sensor arrangement 1 in a schematically simplified cross-sectional view. Shown is a stacked arrangement 5 of an illuminating means 3 in the form of a light emitting diode, a frequency-selective optical element 6 and a photodiode 4 on a carrier substrate 2. The overlapping direction 10 of the stacked arrangement 5 corresponds to the direction of the surface normal of the carrier substrate 2. Here, seen in the main radiation direction 9, the illuminating means 3 lies above the frequency-selective optical element 6, which in turn is arranged above the photodiode 4.

The stacked arrangement 5 is laterally enclosed by a reflective material 11 in concave mirror form and an optical barrier 19 in such a way that electromagnetic radiation from the upper side 13 of the illuminating means 3 can take place in the main radiation direction 10. The frequency-selective optical element 6 arranged on the back side of the illuminating means 3 comprises a divider mirror 7 in the form of a Bragg mirror whose maximum reflectivity is for a wavelength corresponding to the wavelength $\lambda_e$ of the maximum of the spectral distribution of the electromagnetic radiation emitted by the illuminating means 3. The further part of the frequency-selective optical element 6 is formed by an optical filter 8 arranged under the divider mirror 7, which is designed as a long-pass filter whose cut-on wavelength $\lambda_c$ is greater than the wavelength $\lambda_e$ of the maximum of the spectral distribution of the electromagnetic radiation emitted by the illuminating means 3.

Figure 2:
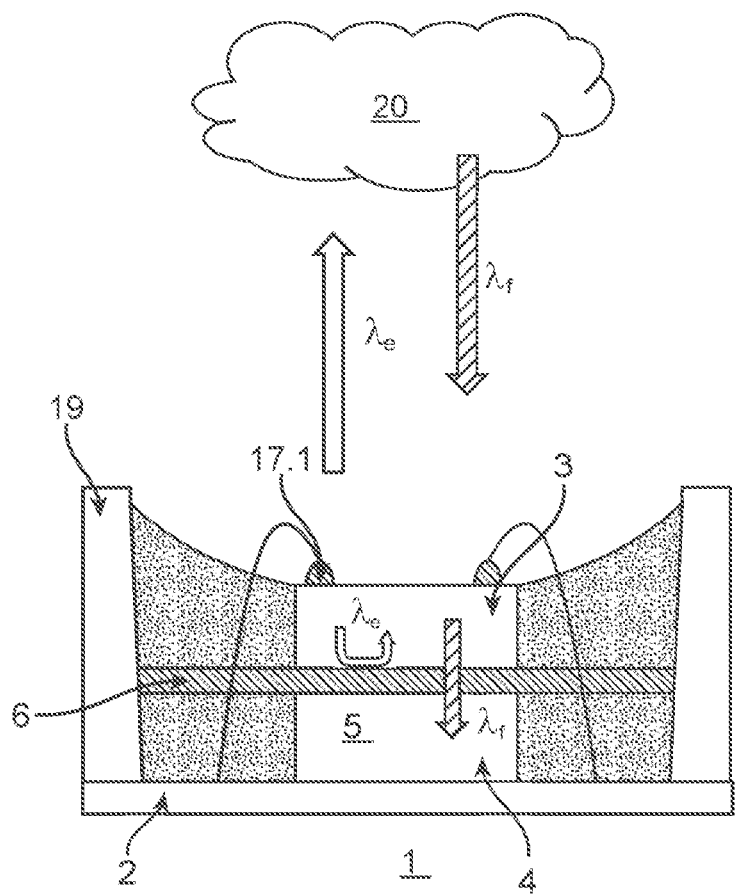
FIG. 2 illustrates the optical measuring method according to embodiments.

The photodetector 4 is enclosed by a layer of electromagnetic radiation-absorbing material 11 and the opaque carrier substrate 2 in such a way that the radiation to be detected reaches the photodetector 4 exclusively through the frequency-selective optical element 6 of the stacked arrangement 5. In this way, the measuring method illustrated in FIG. 2 can be realized.

Figure 3:
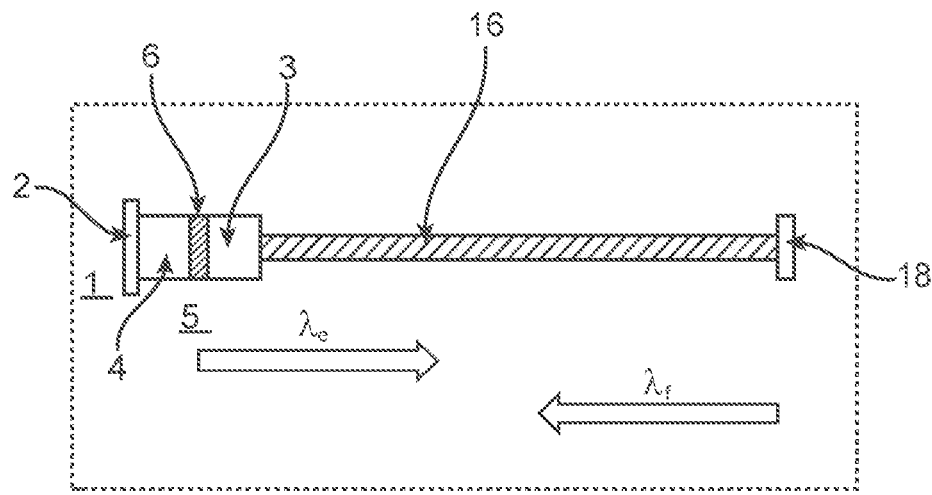
FIG. 3 shows an optical measuring device according to Embodiments.

The illumination of a measuring object 20 by the illuminating means 3 is shown with a spectral distribution whose maximum lies at a wavelength of $\lambda_e$. At least a portion of the light backscattered by the measuring object 20 comprises a wavelength of $\lambda_f$ which is frequency shifted with respect to the wavelength $\lambda_e$, wherein $\lambda_f > \lambda_e$ is assumed. By choosing the cut-on wavelength $\lambda_c$ of the optical filter 8 to be $\lambda_f > \lambda_c > \lambda_e$, only the light backscattered from the measuring object 20 reaches the photodetector 4. If the optical measuring device shown schematically simplified in FIG. 3 is used for the measurement with a fiber-optic element 16 to which an optoelectronic sensor arrangement 1 is optically coupled, the frequency shift of the backscattered radiation with wavelength $\lambda_f$ depends on the strain state of the fiber-optic element 16, which can be determined by the signal at the photodetector 4.

Figure 4:
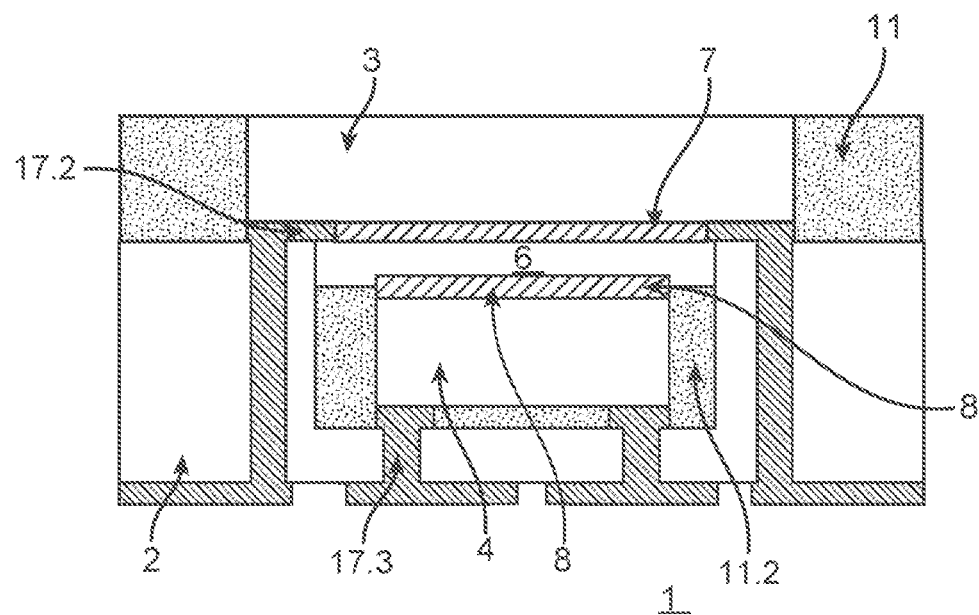
FIG. 4 a cross-sectional view of a second embodiment of the optoelectronic sensor arrangement.

FIG. 4 shows a schematically simplified cross-sectional view of a second embodiment of the optoelectronic sensor arrangement 1. The same reference signs are used for the components corresponding to the first embodiment. The arrangement of the photodetector 4 in a cavity of the carrier substrate 2 is shown, which is covered by the divider mirror 7 of the frequency-selective element 6 and the illuminating means 3 in such a way that all the radiation incident on the photodetector 4 must pass through the illuminating means 3 and the frequency-selective optical element 6.

The contacting 17.2 of the illuminating means 3 is from the back side, so that a flip-chip mounting element can be used. Accordingly, the photodetector 4 can be formed by a flip-chip mounting element if, as shown in FIG. 4, the contacting 17.3 from the carrier substrate back side is realized by a via connection in the bottom of the cavity.

Figure 5:
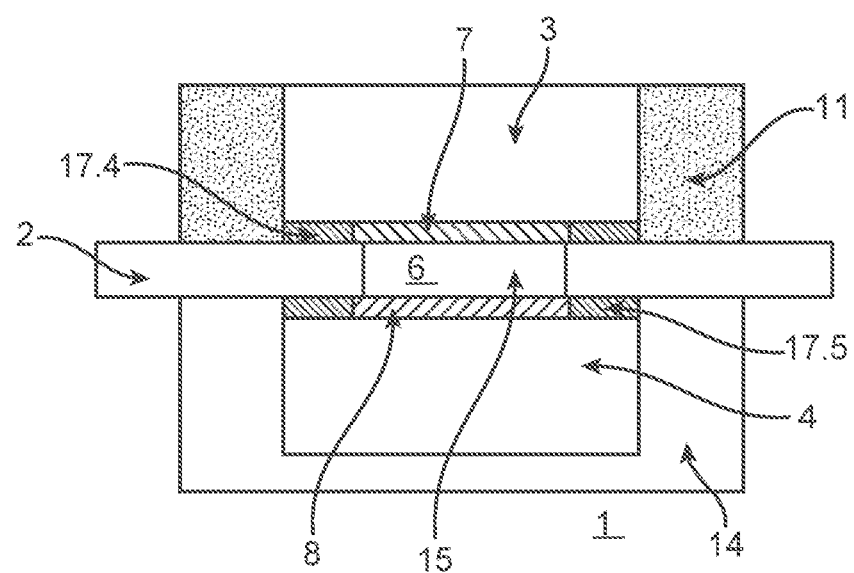
FIG. 5 a cross-sectional view of a third embodiment of the optoelectronic sensor arrangement.

FIG. 5 shows a schematically simplified cross-sectional view of a third embodiment of the optoelectronic sensor arrangement 1. This has an arrangement of the illuminating means 3 on a first side of the carrier substrate 2, while the photodetector 4 is placed on the opposite substrate side. Accordingly, the carrier substrate 2 is additionally part of the stacked arrangement 5, which comprises the illuminating means 3, the frequency-selective optical element 6 and the photodetector 4. In this case, the photodetector 4 is surrounded by an opaque component made of an electromagnetic radiation-absorbing material 14 and radiation can only enter the measuring area through an optical window 15 in the carrier substrate 2, which is covered by the illuminating means 3 and the frequency-selective optical element 6. For the shown embodiment, the illuminating means 3 and the photodetector 4 can advantageously be realized by flip-chip mounting elements, the contacts 17.4 and 17.5 of which originate from the respective assigned side of the carrier substrate 2.

Although the invention has been illustrated and described in detail by means of the preferred embodiment examples, the present invention is not restricted by the disclosed examples and other variations may be derived by the skilled person without exceeding the scope of protection of the invention.

The invention claimed is:

1. An optoelectronic sensor arrangement comprising:
a carrier substrate;
an illuminating device;
a frequency-selective optical element; and
a photodetector,
wherein the illuminating device and the photodetector form a stacked arrangement on or with the carrier substrate,
wherein the frequency-selective optical element is arranged between the illuminating device and the photodetector,
wherein the photodetector is arranged in a cavity of the carrier substrate, which is covered by the illuminating device and/or the frequency-selective optical element, and
wherein the frequency-selective optical element comprises a divider mirror and an optical filter.

2. The optoelectronic sensor arrangement according to claim 1, wherein the photodetector is located rearwardly of the illuminating device such that electromagnetic radiation received by the photodetector passes through the illuminating device before reaching the photodetector.

3. The optoelectronic sensor arrangement according to claim 1, wherein the frequency-selective optical element is configured to shield the photodetector from electromagnetic radiation emitted by the illuminating device.

4. The optoelectronic sensor arrangement according to claim 1, wherein the divider mirror is a Bragg mirror whose maximum reflectivity is at a wavelength corresponding to a wavelength $\lambda_e$ of a maximum of a spectral distribution of electromagnetic radiation emitted by the illuminating device.

5. The optoelectronic sensor arrangement according to claim 1, wherein the optical filter is a long-pass filter whose cut-on wavelength $\lambda_c$ is greater than a wavelength $\lambda_e$ of a maximum of a spectral distribution of electromagnetic radiation emitted by the illuminating device.

6. The optoelectronic sensor arrangement according to claim 1, wherein the illuminating device is arranged in a direction of its main radiation direction above the photodetector.

7. The optoelectronic sensor arrangement according to claim 1, wherein an overlapping direction of the stacked arrangement is oriented in a direction of a surface normal of the carrier substrate.

8. The optoelectronic sensor arrangement according to claim 1, wherein the photodetector is surrounded by the carrier substrate and/or an electromagnetic radiation-absorbing material such that radiation received by the photodetector passes exclusively through the frequency-selective optical element.

9. The optoelectronic sensor arrangement according to claim 1, wherein the illuminating device is embedded in a reflective material.

10. The optoelectronic sensor arrangement according to claim 1, wherein the illuminating device is an optoelectronic surface emitter or an optoelectronic edge emitter.

11. The optoelectronic sensor arrangement according to claim 10, wherein the illuminating device is a light-emitting diode or a laser-emitting diode.

12. The optoelectronic sensor arrangement according to claim 1, wherein the illuminating device and the photodetector are arranged on the same side of the carrier substrate.

13. The optoelectronic sensor arrangement according to claim 1, wherein the illuminating device and the photodetector are located on different sides of the carrier substrate and an optical window is arranged in the carrier substrate between the illuminating device and the photodetector.

14. The optoelectronic sensor arrangement according to claim 1, wherein the illuminating device and/or the photodetector is a flip-chip mounting element.

15. An optical measuring device comprising:
a fiber-optic element optically coupled to the optoelectronic sensor arrangement according to claim 1.

16. An optical measuring method, the method comprising:
coupling electromagnetic radiation generated by an illuminating device arranged on a carrier substrate into a fiber-optic element; and
returning at least a portion of the radiation backscattered in the fiber-optic element to a photodetector, which forms a stacked arrangement with the illuminating device on or with the carrier substrate,
wherein the photodetector is located rearwardly of the illuminating device such that the electromagnetic radiation received by the photodetector passes through the illuminating device and through a frequency-selective optical element arranged between the illuminating device and the photodetector before reaching the photodetector.

17. The method according to claim 16, wherein the frequency-selective optical element exclusively transmits electromagnetic radiation, which is frequency-shifted with respect to the electromagnetic radiation emitted by the illuminating device.

18. The method according to claim 16, wherein a wavelength of the backscattered radiation depends on an elongation state of the fiber-optic element.

* * * * *